United States Patent
Wilson et al.

(10) Patent No.: US 11,529,438 B2
(45) Date of Patent: Dec. 20, 2022

(54) POROUS CARRIER MATRIX

(71) Applicant: Bioventus, LLC, Durham, NC (US)

(72) Inventors: Christopher Wilson, Auburndale, MA (US); Eric Vanderploeg, Stoneham, MA (US); Cheryl Lee, Brighton, MA (US); Chase Davis, Santa Margarita, CA (US); Howard Seeherman, Cambridge, MA (US); John Wozney, Hudson, MA (US)

(73) Assignee: BIOVENTUS, LLC, Durham, NC (US)

( * ) Notice: Subject to any disclaimer, the term of this patent is extended or adjusted under 35 U.S.C. 154(b) by 582 days.

(21) Appl. No.: 16/445,745

(22) Filed: Jun. 19, 2019

(65) Prior Publication Data

US 2019/0388585 A1    Dec. 26, 2019

Related U.S. Application Data

(60) Provisional application No. 62/689,611, filed on Jun. 25, 2018.

(51) Int. Cl.

| | |
|---|---|
| *A61L 27/42* | (2006.01) |
| *A61L 27/56* | (2006.01) |
| *A61L 27/54* | (2006.01) |
| *A61L 27/24* | (2006.01) |
| *A61L 31/16* | (2006.01) |
| *A61L 27/46* | (2006.01) |
| *A61L 27/32* | (2006.01) |

(52) U.S. Cl.
CPC ............ *A61L 27/425* (2013.01); *A61L 27/24* (2013.01); *A61L 27/54* (2013.01); *A61L 27/56* (2013.01); *A61L 27/32* (2013.01); *A61L 27/46* (2013.01); *A61L 31/16* (2013.01); *A61L 2300/606* (2013.01); *A61L 2430/02* (2013.01)

(58) Field of Classification Search
CPC ..... A61L 27/425; A61L 27/12; A61L 26/0033
See application file for complete search history.

(56) References Cited

U.S. PATENT DOCUMENTS

| | | |
|---|---|---|
| 8,952,131 B2 | 2/2015 | Berasi et al. |
| 2007/0041906 A1* | 2/2007 | Lidgren ................. A61K 33/06 424/9.4 |
| 2016/0184390 A1 | 6/2016 | Vanderploeg et al. |
| 2017/0197833 A1 | 7/2017 | De Gasparo et al. |
| 2017/0319750 A1* | 11/2017 | Grinberg ................. A61L 27/58 |

OTHER PUBLICATIONS

Hermida et al., J. Ortho Surg. Res., 2010, 5:57, 8 pages.*
Osidak et al., Russian J Gen Chem, 2014, 84/2, 368-378.*

* cited by examiner

*Primary Examiner* — Kyle A Purdy
(74) *Attorney, Agent, or Firm* — Barnes & Thornburg LLP

(57) ABSTRACT

Medical devices, substrates and biologic therapies for bone repair and guided tissue regeneration are disclosed. More particularly, bone graft substitutes and bone void fillers which comprise a porous collagen matrix and calcium deficient hydroxyapatite ceramic granules for delivery of osteoinductive or other therapeutic agents are disclosed.

6 Claims, 6 Drawing Sheets

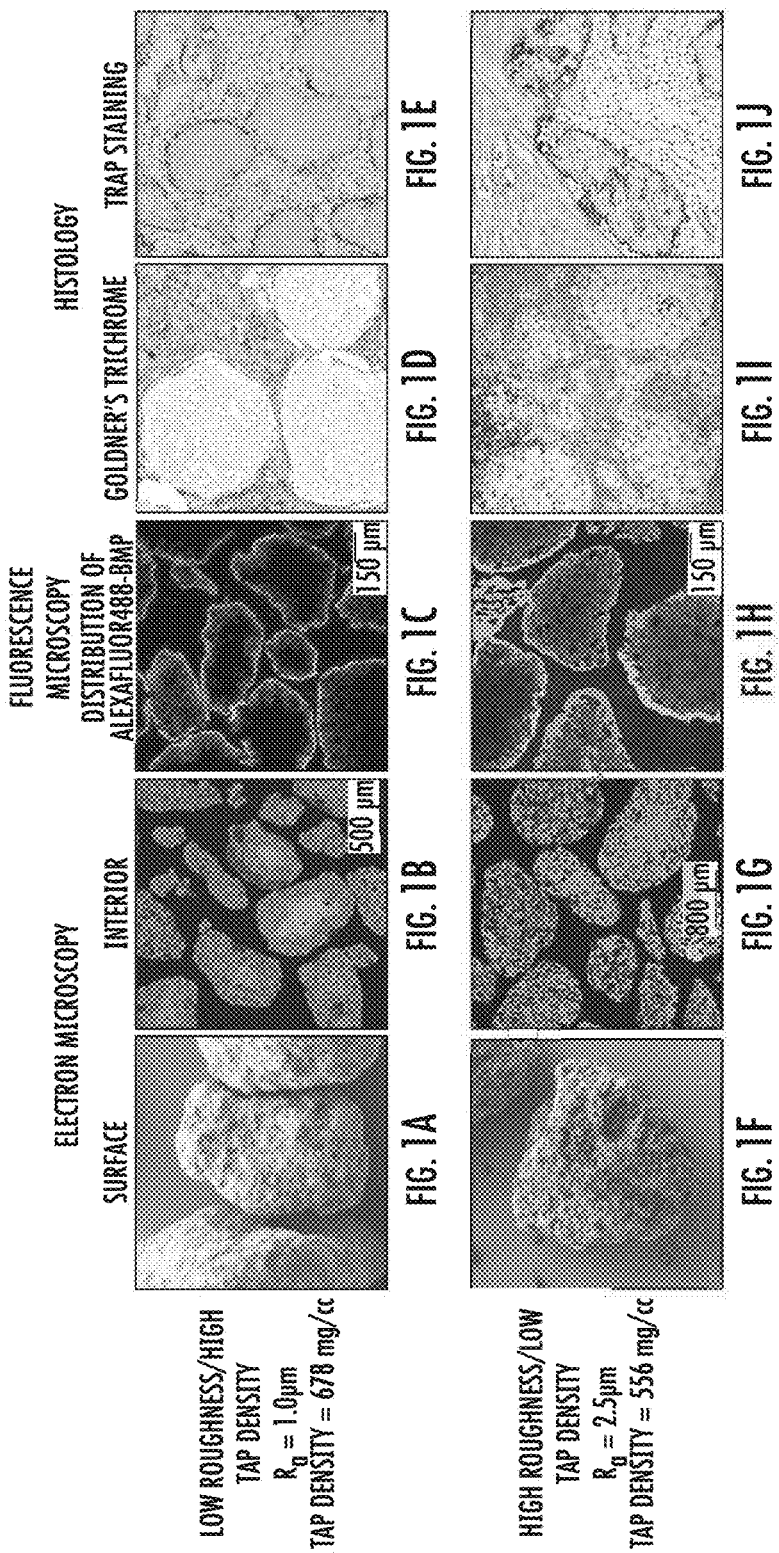

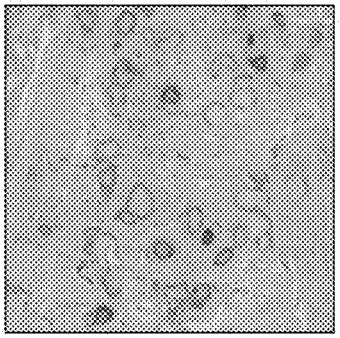
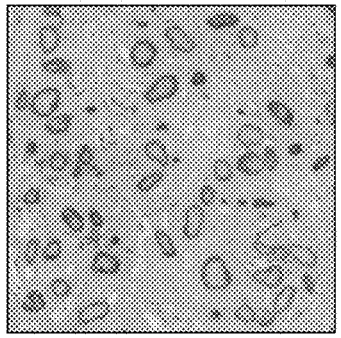
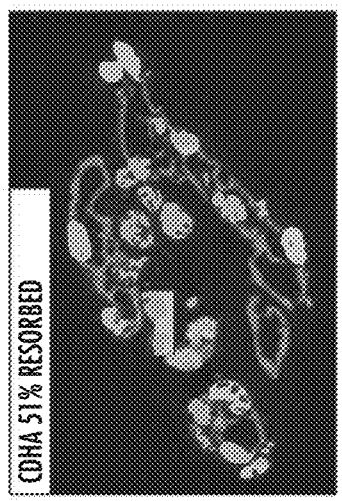
RAT IMPLANTS
6 WEEKS POST-OP
MICROCOMPUTED TOMOGRAPHY
NONHUMAN PRIMATE IMPLANTS
6 MONTHS POST-OP
HISTOLOGY - TRAP STAINING
CDHA 8% RESORBED
FIG. 2A
FIG. 2B
LOW ROUGHNESS/HIGH TAP DENSITY
$R_a = 1.7 \mu m$
TAP DENSITY = 755 mg/cc
CDHA 51% RESORBED
FIG. 2C
FIG. 2D
HIGH ROUGHNESS/LOW TAP DENSITY
$R_a = 2.7$-$2.9 \mu m$
TAP DENSITY = 588-625 mg/cc

POROUS CARRIER MATRIX

FIELD OF THE INVENTION

This application relates to medical devices and biologic therapies, and more particularly to substrates for bone repair which include protein-loaded matrices. More particularly, this application relates to bone graft substitutes and bone void fillers for delivery of osteoinductive or other therapeutic agents, which comprise a porous collagen matrix and calcium deficient hydroxyapatite ceramic granules that provide for guided tissue regeneration.

BACKGROUND

Bone grafts are used in roughly two million orthopedic procedures each year, and generally take one of three forms. Autografts, which typically consist of bone harvested from one site in a patient to be grafted to another site in the same patient, are the benchmark for bone grafting materials, inasmuch as these materials are simultaneously osteoconductive (it serves as a scaffold for new bone growth), osteoinductive (promotes the development of osteoblasts) and osteogenic (contains osteoblasts which form new bone). However, limitations on the supply of autografts have necessitated the use of cadaver-derived allografts. These materials are less ideal than autografts, however, as allografts may trigger host-graft immune responses or may transmit infectious or prion diseases, and are often sterilized or treated to remove cells, eliminating their osteogenicity.

The biological properties of bone graft substitutes are often described by the terms osteoinductivity, osteoconductivity and osteogenicity. Osteoinductivity is the ability of a graft to actively stimulate or promote bone formation. Osteoconductivity is a property of the scaffold that allows the colonization and ingrowth of new bone cells and sprouting capillaries due to its three-dimensional structure. Osteoconduction is mainly determined by the porosity properties of the scaffold and also to a lesser extent by the chemical and physical properties of the substrate that promote adhesion and cell growth. The mechanical properties of bone graft materials and their resistance to compression and torsion are dependent in part, on their composition and porosity.

Significant technical challenges have prevented the efficient incorporation of osteoinductive materials into synthetic bone graft substitutes and controlled release of osteoinductive materials from the implant which, in turn, has limited the development of high-quality osteoinductive synthetic bone graft materials. Moreover, necessary sterilization of synthetic bone graft compositions and inefficient or inconsistent crosslinking of bone graft matrices have resulted in bone grafts having weakened or less than desirable mechanical properties. There is, therefore, a need for synthetic bone graft compositions having consistent and robust mechanical properties and biological properties that promote bone growth at the site of implant.

SUMMARY OF THE INVENTION

The present invention addresses the shortcomings of current-generation synthetic bone grafts by providing graft materials with improved loading of osteoinductive materials, as well as methods of making and using the same.

In one aspect of the invention, there is provided a porous calcium-deficient hydroxyapatite (CDHA) granule comprising macropores and micropores, said granule having a diameter ranging in size from 425 to 800 μm, and having a specific surface area of greater than 50 $m^2/g$, a surface roughness (Ra) of at least 2.2 μm, and a pH of 3.5 to 6.5.

In another aspect, the invention provides a composition comprising a plurality of porous CDHA granules comprising macropores and micropores, said granules having a diameter in the range of from 425 to 800 μm, a surface roughness (Ra) of at least 2.2 μm and a pH of 3.5 to 6.5; and wherein said plurality of granules has a tap density of less than 700 mg/cc; wherein said plurality of granules is admixed with a biocompatible matrix comprising an acidic collagen gel and an alkaline collagen powder, and wherein the collagen gel and collagen powder are present in the biocompatible matrix at a 1:1 ratio by dry mass. In certain embodiments, the granules have a specific surface area of greater than 50 $m^2/g$.

In yet another aspect, there is provided a bone graft substitute comprising a biocompatible porous carrier matrix comprising an acidic collagen gel and an alkaline collagen powder, wherein the collagen gel and collagen powder are present in the biocompatible matrix at a 1:1 ratio by dry mass and are cross-linked, said matrix having admixed therein a plurality of porous CDHA granules having a tap density of less than 700 mg/cc, and wherein said granules have a diameter in the range of from 425 to 800 μm, a surface roughness (Ra) of at least 2.2 μm and a pH of 3.5 to 6.5; and wherein said bone graft substitute is sterilized via exposure to E-Beam irradiation or ethylene oxide. In certain embodiments, the granules have a specific surface area of greater than 50 $m^2/g$.

Also provided are methods of making a porous carrier matrix comprising the steps of:
a. Forming a two-phase Type I collagen mixture comprising a water-swelled acidic collagen gel and an alkaline collagen powder, and adjusting the mixture to an isotonic condition and neutral pH to form a biocompatible matrix material; wherein said collagen gel and collagen powder are mixed at a 1:1 ratio by dry weight;
b. Adding a plurality of porous CDHA granules having a tap density of less than 750 mg/cc to said biocompatible matrix material to form a composite slurry, wherein said CDHA granules have a diameter of from 425-800 μm and comprise macropores and micropores, a surface roughness ($R_a$) of at least 2.2 μm, and a pH of 3.5 to 6.0.;
c. Shaping said composite slurry into a desired size and shape to form a shaped composite slurry and lyophilizing the shaped composite slurry to form a lyophilized composite material;
d. Rehydrating the lyophilized composite material to form a rehydrated composite material and adding a cross-linking agent to the rehydrated composite material to form a cross-linked composite material; and
e. Lyophilizing and sterilizing the cross-linked composite material via exposure to E-Beam or ethylene oxide to form a sterilized composite material.

In certain embodiments of this aspect of the invention, the cross-linking agent is glutaraldehyde or Ethyl-3-[3-dimethylaminopropyl]carbodiimide (EDC). In certain embodiments, the method of making a porous carrier matrix further comprises a step of exposing the sterilized composite material to a solution comprising an osteoinductive material under conditions sufficient to adhere the osteoinductive material to a plurality of the micropores and macropores and the outer surface of the granules.

BRIEF DESCRIPTION OF THE DRAWINGS

Certain embodiments of the present invention are illustrated by the accompanying figures. It will be understood that details not necessary for an understanding of the invention or that render other details difficult to perceive may be omitted. It will be understood that the invention is not necessarily limited to the particular embodiments illustrated herein.

FIGS. 1A-J demonstrate differences between CDHA granules prepared with low surface roughness ($R_a$) and high tap density (top row; FIGS. 1A-1E) and high surface roughness and low tap density (bottom row, FIGS. 1F-1J). FIGS. 1A and 1F are electron micrographs showing surface architecture of the granules; FIGS. 1B and 1G are electron micrographs showing the internal architecture of the granules; FIGS. 1C and 1H are fluorescence micrographs showing the spatial distribution of an osteogenic biologic within the granules; FIGS. 1D, 1E, 1I and 1J are thin sections of implanted granules showing the colonization of implanted granules by mesenchymal cells and osteoclasts. FIGS. 1D and 1I show histologic evaluation of implanted granules via staining with Goldner's trichrome. FIGS. 1E and 1J show histologic evaluation of implanted granules via staining thin sections of the granules for tartrate-resistant alkaline phosphatase (TRAP) activity.

FIG. 2 shows thin sections of implanted granules. FIGS. 2A and C are thin sections visualized by microcomputed tomography. FIGS. 2B and 2D are thin sections of implanted granules stained for TRAP activity.

FIG. 3 shows the relationship of tap density to wetting capacity and retention of osteogenic materials by CDHA granules.

FIG. 4 shows the tensile properties and geometric stability of collagen/CDHA implants of the invention.

FIG. 5 shows the relationship of the cross-linking agent used to prepare the implants of the invention to amount of osteogenic material released from the implants in vitro.

DETAILED DESCRIPTION

Figure 3A:
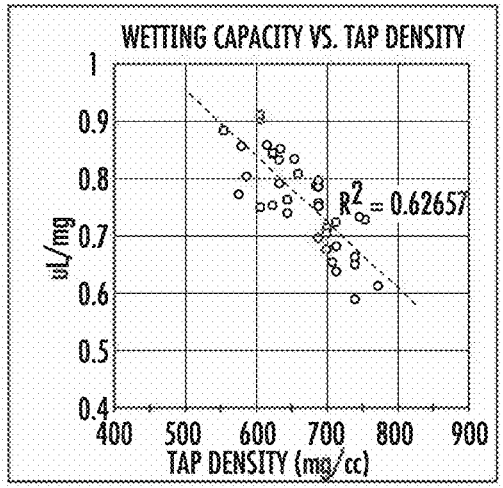
FIG. 3A is a plot of wetting capacity versus tap density.

Implants (also referred to as "constructs") according to the various embodiments of the present invention generally include three components: an osteoconductive material, such as a calcium ceramic or other solid mineral body, an osteoinductive material such as a bone morphogenetic protein, and a biocompatible matrix material that reacts to form a gel or other mass. As used herein, osteoconductive materials refer to any material which facilitates the ingrowth of osteoblastic cells including osteoblasts, micro-pores and macro-pores increase the total surface area to which the osteoinductive substance can adhere, but only the macro-pores permit infiltration by cells. Thus, osteoinductive substance within the micro-pores becomes available only gradually via elution or as the granule is degraded by cells infiltrating the macro-pores.

The CDHA granules have an architecture appropriate to allow an implant of the invention to remain in place and to release osteoinductive material over time intervals optimal for the formation and knitting of bone (e.g., days, weeks, or months), and to allow the in-growth of osteoblastic cells. The porosity of the CDHA granules is selected to achieve desired granule residence times or kinetics of release of osteoinductive materials. Microporosity generally refers to the existence of pores with a relatively narrow average diameter that is nonetheless large enough to permit infiltration of fluids such as BMP-loaded solutions into micropores without immediately contacting a surface of the micropore sufficiently large to permit fluid access without excessive surface tension). Macroporosity, with respect to granules, generally refers to the existence of pores sized to permit infiltration by cells. In general, the CDHA granules include micropores having a diameter in the range of from 3 to 35 µm, preferably from 5 to 30 µm, more preferably from 10 to 15 µm and a fewer number of macropores in the range of from 50 to 100 µm.

The CDHA granules used in the compositions and implants of the invention also have a high surface area, which ensures maximal uptake and absorption of the osteoinductive material into the granules. In some embodiments, the specific surface area of the granules is greater than 40 $m^2/g$, and in preferred embodiments, the specific surface area is greater than 50 $m^2/g$. In general, the specific surface area is less than about 90-100 $m^2/g$.

The inventors' studies have shown that the surface roughness of the CDHA granules significantly affects the ability of cells to invade the granules and thereby regenerate bone at the site and affects resorption of the granules. In preferred embodiments, the CDHA granules have a high surface roughness as measured by microscopy, providing an open surface where a plurality of pores is open to the outer surface of the granule. The surface roughness of the CDHA granules used in the compositions and implants of the invention is at least 1.3 µm, as measured microscopically. The inventors have discovered that cell invasion of implanted constructs and osteoclast activity is positively related to surface roughness of the CDHA granules used in the implants. Cell Invasion (CI) scoring of CDHA granules indicates that maximal cell invasion is detected for granules having an $R_a$ greater than 1.3 µm, preferably greater than 2.0 µm, and more preferably, an $R_a$ of at least 2.2 µm, more preferably greater than 2.5 µm. (FIG. 6).

The inventors' studies have also shown that CDHA granules having an acidic pH demonstrate an increased uptake of osteoinductive material into the interior of the granules. Increasing the amount of osteoinductive material in the interior of the granules results in a slower and more controlled release of the osteoinductive material from the granules. By controlling the pH of the granules, it is possible to maintain the pH of granule-containing compositions and implants below pH 7.0, and thereby draw osteoinductive materials into the compositions and implants. Preferably, the pH of the granules is between 3.5 to 6.5, more preferably between 5.5 and 6.5. This pH range has been shown to facilitate the penetration of osteoinductive material such as BMP into the interior pore structure of the granules. (See US Pat. App. No. 20160184390 for example, incorporated herein by reference).

The inventors' studies have also shown that the tap density of the CDHA granules has a significant effect on the properties of the granules. The tap density of a powdered material is an increased bulk density attained after mechanically tapping a container containing a powder sample. For granules of a given size range, the tap density is a surrogate metric for the wetting capacity of the granules, i.e., the capacity of the granules to take up a solution, such as a solution containing a biological compound. The inventors' studies show that a low tap density of CDHA granules results in a higher wetting capacity, which results in more material, e.g., osteoinductive material, being drawn into the granules and a higher retention of osteoinductive material in the granules; a more uniform intra-granule distribution of osteoinductive material; and overall improved retention of osteoinductive material. A low tap density of the granules ensures that sufficient osteoinductive material or drug, for example, is drawn into the interior pores of the ceramic granules. Preferably, the CDHA granules used in the compositions and implants of the invention have a tap density of less than 700 mg/cc, more preferably less than 650 mg/cc or less than 600 mg/cc.

Osteoinductive materials included in the compositions and implants of the invention generally include for example, peptide and non-peptide growth factors that stimulate the generation of, or increase the activity of, osteoblasts and/or inhibit the activity or generation of osteoclasts. In some embodiments, the osteoinductive material is a member of the transforming growth factor beta (TGF-β) superfamily such as TGF-β. More preferably, the osteoinductive material is a bone morphogenetic protein (BMP) such as BMP-2, BMP-3, BMP-4, BMP-5, BMP-6, BMP-7, BMP-9, or a designer BMP such as the BMP-GER or BMP-GER-NR chimeric BMPs described in U.S. Pat. No. 8,952,131 by Berasi et al. entitled "Designer Osteogenic Proteins," the entire disclosure of which is hereby incorporated by reference for all purposes. In other embodiments, the osteoinductive material is a fibroblast growth factor, insulin-like growth factor, platelet-derived growth factor, a small molecule, a nucleotide, a lipid, or a combination of one or more of the factors listed herein. In preferred embodiments, the compositions and implants include a BMP, preferably BMP-2 or BMP-GER-NR.

Various embodiments of the invention utilize a biocompatible matrix, which when used with the CDHA granules, exhibits sufficient rigidity and/or column strength to withstand the loads placed upon it when implanted. The matrix used in the compositions and implants of the invention does not cause excessive inflammation (i.e., inflammation sufficient to inhibit or prevent the formation of new bone or the knitting of a broken bone), inhibit the proliferation of osteoblasts, or otherwise interfere with the activity of the granules and/or the osteoinductive material; and has sufficient cohesion over an appropriate interval to permit the deposition of new bone. In addition, the biocompatible matrix is optionally biodegradable and/or osteoconductive.

In various embodiments, the biocompatible matrix comprises collagen. In certain embodiments, the matrix contains a two-phase type 1 collagen mixture, such as a bovine type 1 collagen mixture, preferably a two-phase type 1 collagen mixture made from a 1:1 (dry mass) mixture of an acidic collagen gel and a milled alkaline collagen powder, such as collagen gel and milled collagen powders available either as standard or custom products from suppliers of animal derived collagen materials for biomedical applications. The mixture of collagens ensures that collagen fibers in the collagen gel become connected by the milled collagen particles, providing a strong, biocompatible, porous matrix.

The collagen mixture is reacted to form a gel or other solid mass, for example, by cross-linking in the presence of the CDHA granules. Suitable cross-linking agents include, for example, glutaraldehyde or 1-Ethyl-3-[3-dimethylaminopropyl]carbodiimide (EDC). Preferably, EDC, a zero-length crosslinking agent, is used to cross-link the collagen mixture. The use of EDC to cross-link the matrix enables a reduction in the amount of collagen necessary for maintaining the integrity of the matrix, while also enabling the use of an increase in the amount of CDHA granules in the matrix. This, in turn, provides for enhanced mechanical and structural integrity of the compositions and implants of the invention and improved retention of osteoinductive material.

The mixture of collagen gel and milled collagen powder comprises approximately 4 to 12% of the compositions and implants of the invention, and preferably about 7 to 8% by dry mass of the compositions and implants. The amount of CDHA granules in the compositions and implants by dry mass is about 88-96%, preferably about 92-93%.

The process by which the two-phase collagen mixture is combined to form a collagen slurry may include a step of mixing the acidic collagen gel with an amount of water, preferably deionized water, to bring the gel to the desired concentration. The diluted acidic collagen gel is mixed to ensure consistency. For example, the collagen gel may be diluted to a final concentration of 0.5 to 2.5%, preferably 0.75-1.5%, more preferably 0.75%, and mixed with a shear mixer such as an overhead shear mixer for several minutes, e.g., 1-10 minutes. The mixture is allowed to swell for up to 21 days, preferably at 4° C. The alkaline collagen powder is then mixed into the swelled collagen gel solution at a 1:1 ratio of dry mass and blended. After about 16-24 hours, preferably at 4° C., the mixture is brought to an isotonic condition and substantially neutral pH (pH 7.0 to 7.6) by the addition of phosphate buffered saline solution, for example, and sodium hydroxide, for example. After a final rest time of about 6-36 hours, such as 16-24 hours, CDHA granules are folded or otherwise mixed into the collagen solution in an appropriate amount, e.g., 120-240 mg/cc, 150-175 mg/cc, 175-200 mg/cc, or 200-225 mg/cc for example, to form a composite slurry. The inventors' studies have shown that an increasing CDHA content within this range results in higher retention of osteogenic material at the implantation site.

The composite slurry (i.e., granules plus collagen mixture) may be manipulated to form an implant of desired size and shape by placing the slurry into a mold of desired shape and size, for example. The mold optionally may be fitted with fixtures that impart through holes (fenestrations) in the final device, for example. The molded slurry is frozen and lyophilized, and then rehydrated in an appropriate liquid medium and crosslinked. As noted above, the cross-linking agent used to cross-link the collagen may be for example, glutaraldehyde for one to two hours, or EDC, e.g., 50 mM EDC in 80% ethanol for two hours for example. The cross-linked and lyophilized product may be washed in water to remove excess cross-linking agent and may be refrozen and lyophilized again.

The resulting lyophilized, cross-linked porous collagen matrix (PCM) product (sponge) is preferably subjected to sterilization. Suitable methods of sterilization include gamma irradiation, E-beam sterilization or ethylene oxide (EO) sterilization, for example. Preferably, E-beam or EO are used to sterilize the PCM. It has been found that EO sterilization improves the structural integrity of glutaraldehyde cross-linked PCMs, and that overall, E-beam sterilization and EO are consistently less destructive than gamma sterilization.

The cross-linked, sterilized PCM sponge may be loaded with an osteoinductive material such as BMP by flowing a solution containing the osteoinductive material over the PCM sponge to permit the material to adhere to various inner and outer surfaces of the granules contained within the sponge. The volume of solution applied to the sponge is, in preferred embodiments, sufficient to fully wet the granules, thereby ensuring that all surfaces (including internal pore surfaces) are contacted by the osteoinductive material. The incubation of the sponge may be over a variety of intervals, temperatures, pressures (as may be necessary to facilitate complete infiltration of micropores) or may otherwise be manipulated in any suitable way to tailor the combination of the osteoinductive material and the granules within the sponge. Infiltration of fluids into the granules is optionally facilitated by the inclusion of one or more surfactants in the solution containing the osteoinductive material.

Loading the PCM with an osteoinductive material may be carried out immediately prior to implantation of the PCM material at a site of injury, e.g., prior to surgery. To that end, there is provided a kit for treating a patient with an osteoinductive material. The kit comprises a first vessel containing a cross-linked, sterilized PCM sponge as described herein above; and a second vessel, which may be configured to fluidly couple to the first vessel, the second vessel containing a solution comprising an osteoinductive material. The kit may further include an instruction set comprising a method of treating a patient, such as a method comprising the steps of flowing the solution into the first vessel, thereby associating the ceramic granules within the sterilized PCM with the osteoinductive material. In certain embodiments, the osteoinductive material is bone morphogenetic protein 2 (BMP-2), BMP-3, BMP-4, BMP-5, BMP-6, BMP-7, BMP-9, a designer BMP such as BMP-GER-NR, fibroblast growth factor, insulin-like growth factor, platelet-derived growth factor, transforming growth factor beta (TGF-β), or a combination thereof.

Implants or constructs of the invention that include the osteoinductive materials, granules and biocompatible matrices as described above, have characteristics that are tailored to the facilitation of bone growth and knitting, which include (a) kinetics of release of osteoinductive materials that are appropriate for the application, (b) residence time appropriate to facilitate but not interfere with new bone formation, (c) macroporosity that permits the infiltration of cells and tissues, including new vascular tissue that accompanies the formation of new bone, and (d) sufficient rigidity/or and compression resistance to withstand loads applied to the implant.

In certain aspects and embodiments of the invention, the PCM sponge, implants or compositions may comprise other materials useful in the treatment of bone, such as antimicrobial additives, antibiotics, bioactive glasses, demineralized bone, calcium phosphate putty, and the like, which are incorporated to facilitate bone growth and repair.

Certain principles of the present invention are illustrated by the following non-limiting examples:

EXAMPLES

Example 1

Effects of Surface Roughness and Tap Density on Wetting Capacity, BMP Distribution and Cell Invasion CDHA granules were prepared as described in US Patent Application No. 2017/0197833, the entirety of which is incorporated herein by reference. Briefly, CDHA granules were prepared with low surface roughness ($R_a$) and high tap density (See FIG. 1A) or high surface roughness and low tap density (FIG. 1B). Preparations yielding granules of low $R_a$ (≤2.0 μm) and high tap density (>650 mg/cc) were accomplished essentially as described, with a liquid to powder ratio of 3.8 mL:g, sodium hydroxide concentration of 2.4 mM, and agitation rate of 1 rpm for the chemical conversion of calcium sulfate anhydrous (CSA) template granules to CDHA granules. Granules with high $R_a$ (>2.0 μm) and low tap density (≤650 mg/cc) were prepared with a 3-50-fold higher liquid to powder ratio (typically, 12.9 mL:g), 10-fold higher concentration of sodium hydroxide (24 mM), and a higher rate of agitation (15 rpm) for the chemical conversion of CSA to CDHA. In some cases, the preparation of high $R_a$/low tap density granules included an exchanges of the chemical conversion reagents after a 2-6 h incubation.

To examine the surface architecture, granules were sputter coated with gold and imaged by scanning electron microscopy. The topography and surface roughness of calcium phosphate granules were investigated using white light interferometry with a S neox interferometry and confocal microscope (Sensofar, Spain) and a 50× objective lens. The mean arithmetic roughness ($R_a$) was computed following analysis of images using dedicated software (SensoSCAN ver 6.1.3, Sensofar, Spain).

To examine the internal architecture, granules were embedded in polymethylmethacrylate and polished sections of the blocks were imaged by reflection electron microscopy.

The spatial distribution of an osteoinductive biologic within the granules was examined by applying an aqueous solution of a bone morphogenetic protein functionalized with the fluorophore AlexaFluor488 to the granules. The granules were then rinsed with water, mounted in gelatin, fixed in formalin, processed for paraffin embedding, and sectioned on a microtome. The sections were imaged by confocal fluorescence microscopy.

The colonization of granules by mesenchymal cells and mineral-resorbing osteoclasts was investigated by histologic evaluation of granules implanted into an intramuscular pouch in rats. After two weeks in vivo, the granules and surrounding tissues were collected, fixed in formalin, decalcified, and prepared for histology. Cells and tissues were identified in thin sections stained with Goldner's trichrome. Osteoclast activity was identified by staining thin sections for tartrate-resistant alkaline phosphatase (TRAP) activity.

As can be seen in FIG. 1, the distribution of BMP throughout the interior and on the outer surface of high surface roughness/low tap density granules (FIGS. 1F, 1G, 1H, 1I and 1J) is significantly greater than that observed for low surface roughness/high tap density granules (FIGS. 1A, 1B, 1C, 1D and 1E).

Histologic evaluation of the in vivo implanted granules shows that cell invasion and osteoclast activity is positively related to surface roughness of the CDHA granules (FIG. 1).

Example 2

Effects of Surface Roughness and Tap Density on Resorption

Resorption of CDHA granules was investigated in collagen/CDHA constructs prepared with granules of low roughness and high tap density (FIGS. 2A and 2B) and with granules of high roughness and low tap density (FIGS. 2C and 2D). Constructs were implanted in rats at intramuscular sites along with BV-265 (a.k.a. BMP-GER-NR) and retrieved 6 weeks post-operatively. The implants were fixed in formalin and mineralized components were visualized by microcomputed tomography (uCT). Quantitative analysis of the uCT images allowed for computation of the fraction of CDHA resorbed relative to pre-implantation constructs. Constructs were also implanted in nonhuman primates (rhesus macaques) with BV-265 for posterolateral fusion of the lumbar spine. After six months, the fusion masses were fixed in formalin, decalcified, embedded in paraffin, sectioned, and stained for tartrate-resistant alkaline phosphatase as an indicator of osteoclast activity.

As shown in in FIGS. 2A and 2C, resorption of CDHA granules is significantly enhanced at six weeks post implantation in constructs containing granules with a high surface roughness and low tap density. As can be seen in FIGS. 2B and 2D, osteoclast activity in constructs containing granules with a high surface roughness and low tap density (FIG. 2D) is significantly higher at six months post implantation than in constructs containing granules with low surface roughness and high tap density (FIG. 2B).

Example 3

Effect of Tap Density on BMP Retention

CDHA granules were prepared as described above over a range of reaction conditions. Tap density was determined by a modified method of USP <616>. Briefly, a defined mass of granules was poured into a graduated cylinder, tapped in a controlled manner a set number of times, and the volume ascertained from the markings on the graduated cylinder. The tap density was computed from the known mass and measured volume of the column of granules. Wetting capacity (a.k.a. water capacity) was determined by applying an excess volume of water to a known mass of granules. After incubation for 15 min, the granules were centrifuged at low speed to separate the granules from excess water not captured by the granules. The saturated granules were re-weighed to determine the change in mass due to water uptake. The wetting capacity is reported as volume of water uptake per unit mass of dry granules. In vitro release of BMP was determined by applying a sub-saturating volume of aqueous solution containing bone morphogenetic protein ("BV-265," a.k.a. BMP-GER-NR) to a fixed quantity of granules (typically 50-100 mg). After incubation for 1 h, 1 mL of buffer composed of phosphate buffered saline with 20% v/v fetal bovine serum was applied to the granules. The granules and buffer were incubated for 24 h at 37 C with mild agitation. After 24 h, the buffer was collected and assayed for BV-265 by an enzyme-linked immunosorbent assay (ELISA) specific for BV-265. The results are reported as quantity of BV-265 released into the buffer as a fraction of the total amount of BV-265 applied to the granules. In vivo retention of BMP was determined by preparing implant materials composed of collagen matrix with CDHA granules of low roughness and low tap density, low roughness and high tap density, or high roughness and low tap density (See FIG. 3C), applying 125I-labeled BV-265 (a.k.a. BMP-GER-NR) to the materials, implanting the materials at an intramuscular site in adult male rats, and longitudinally measuring the radioactivity at the implantation site by planar scintigraphy. Data are reported as activity retained at the implantation as a fraction of the activity measured post-operatively.

Figure 3B:
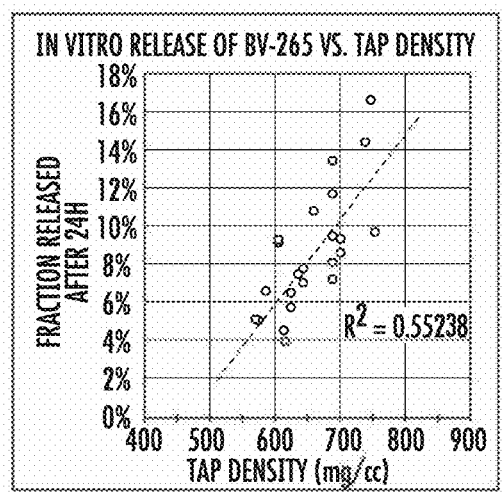
FIG. 3B is a plot of in vitro release of osteogenic material (BV-265) versus tap density.
Figure 3C:
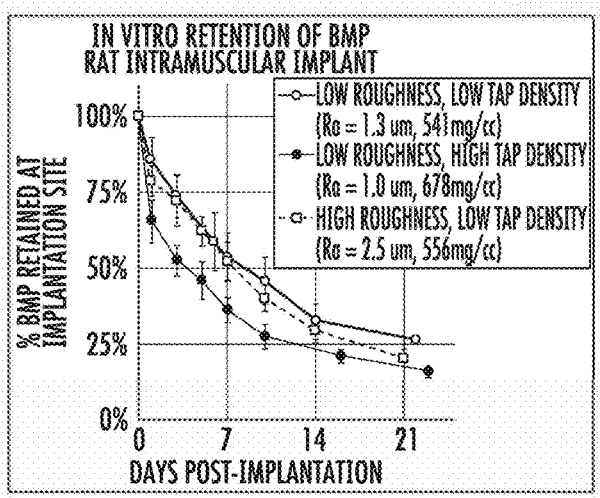
FIG. 3C is a graph showing per cent osteogenic material retained at the implant site over time for implants comprising granules having various combinations of tap density and surface roughness.

As shown in FIG. 3A, wetting capacity of CDHA granules inversely correlates with a tap density, i.e. higher wetting capacity is associated with lower tap density. FIGS. 3B and 3C demonstrate that the release of BMP from CDHA granules in vivo correlates with the release of BMP observed in vitro in regard to tap density. The data shown in FIG. 3C demonstrate that CDHA granules with a low tap density provide significantly greater retention of BMP at the implant site than granules with a high tap density.

Example 4

Effects of Cross-linking Chemistry and Methods of Sterilization on In Vivo Stability and Mechanical Properties of Granules Constructs comprised of bovine type I collagen and CDHA granules (parent slurry comprised of 1.5% w/v bovine type I collagen and 150 mg/cc CDHA granules) were crosslinked with either 0.3 mM glutaraldehyde or 50 mM 1-ethyl-3-(3-dimethylaminopropyl)carbodiimide (EDC) and terminally sterilized by gamma irradiation (25-35 kGy), E-beam irradiation (two exposures of 15 kGy), or exposure to ethylene oxide (EO). The tensile properties of pre-sterile (control) and sterilized sponges were evaluated with a uniaxial tension test in which the constructs were partially hydrated and ramped to failure. The peak stress was computed by dividing the maximum force generated during the test by the cross-sectional area of the construct. The in vivo geometric stability of collagen/CDHA constructs cross-linked with either glutaraldehyde or EDC and sterilized with gamma, E-beam, or EO was evaluated by implanting the constructs in rat intramuscular pouches along with 0.3 mg/mL BV-265 (a.k.a. BMP-GER-NR, a chimeric BMP closely related to BMP-2 and BMP-6) osteoinductive biologic. After two weeks, the implants were retrieved, fixed in formalin, and imaged by microcomputed tomography (uCT) to visualize the mineralized portions of the implants. A moment of inertia was computed for each implant to quantify the spread between CDHA granules, where higher moments of inertia indicate a greater spread, and thus inferior geometric stability, of the construct.

Figure 4A:
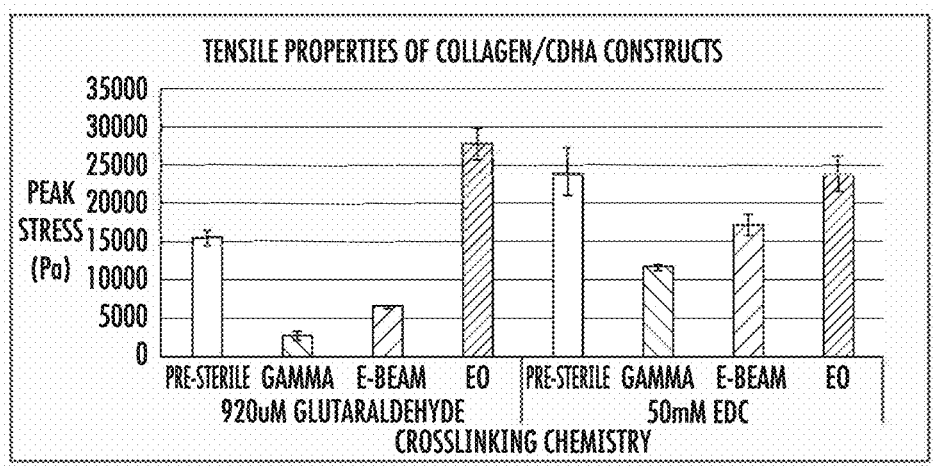
FIG. 4A is a bar graph showing the effects of cross-linking chemistry on the tensile properties of implants sterilized by various means.
Figure 4B:
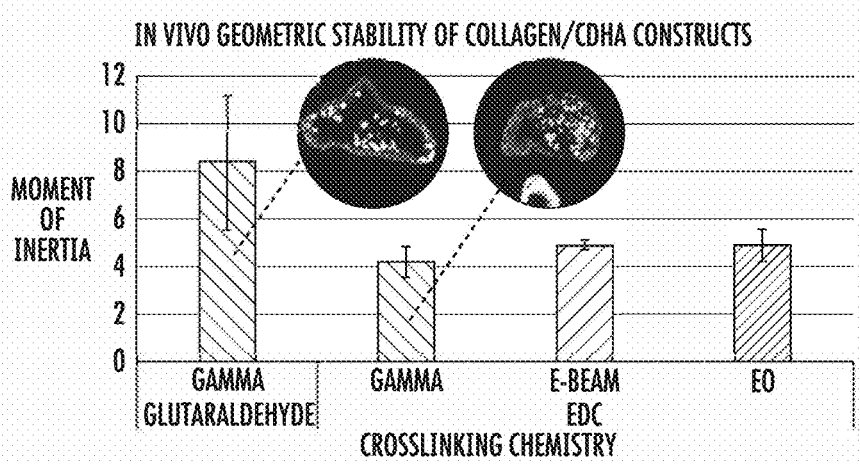
FIG. 4B is a bar graph showing the effects on geometric stability of cross-linking chemistry of implants sterilized by various mean.

As can be seen in FIG. 4A, EDC cross-linking of CDHA/collagen constructs results in significantly better tensile properties than similar constructs cross-linked with glutaraldehyde, regardless of whether sterilization is carried out by gamma-irradiation or E-beam. Surprisingly, FIG. 4A shows that EO sterilization improves the tensile properties of a glutaraldehyde cross-linked construct. FIG. 4B shows that glutaraldehyde-crosslinked, gamma-irradiated constructs have significantly lower geometric stability in vivo than EDC cross-linked constructs, regardless of the method used to sterilize the EDC cross-linked constructs (e.g., gamma-irradiation, E-beam or EO sterilization).

Example 5

Figure 5A:
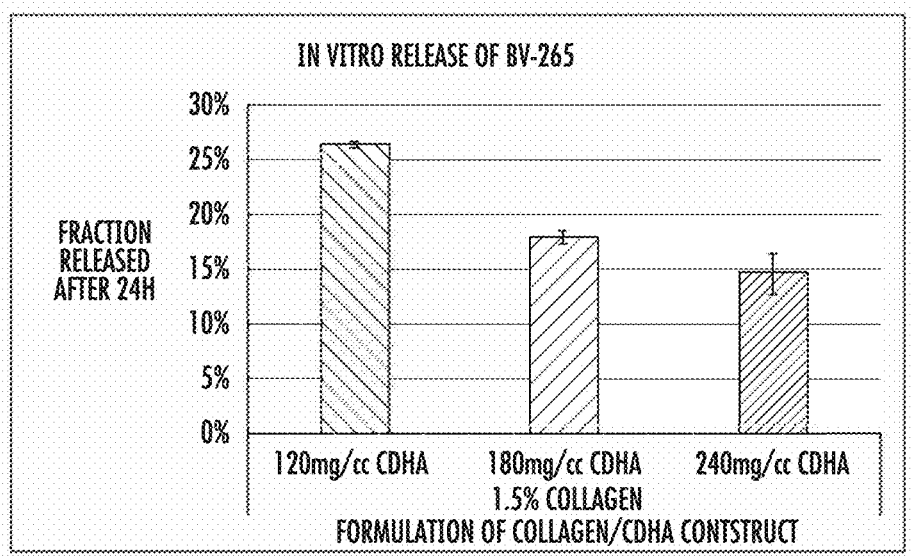
FIG. 5A is a bar graph showing fraction of osteogenic material released after 24 hours from glutaraldehyde cross-linked compositions containing 1.5% collagen and various amounts of granules.
Figure 5B:
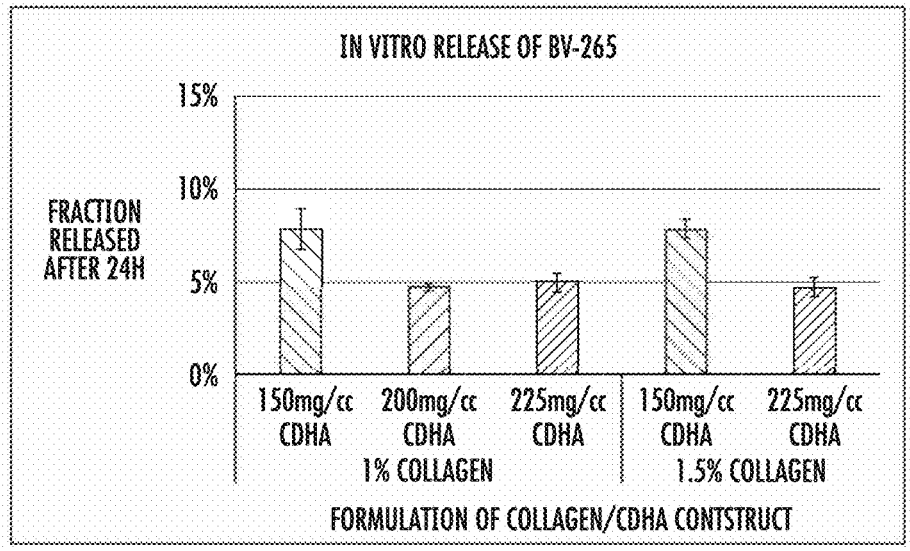
FIG. 5B is a bar graph showing fraction of osteogenic material released after 24 hours for EDC cross-linked compositions containing either 1% or 1.5% collagen and various amounts of granules.

Effects of Cross-linking Chemistry and Ceramic Content on Osteoinductive Material Release Collagen/CDHA constructs were prepared with various collagen and CDHA contents as described above and cross-linked with glutaraldehyde and sterilized by gamma irradiation (FIG. 5A) or crosslinked with EDC and sterilized by E-Beam irradiation (FIG. 5B). In vitro release of chimeric BMP (BV-265; BMP-GER-NR) was determined by applying a sub-saturating volume of aqueous solution containing BV-265 to a fixed geometry of construct (typically, 6 mm diameter×8 mm high). After incubation for 1 h, 1 mL of buffer composed of phosphate buffered saline with 20% v/v fetal bovine serum was applied to the construct in a tube. The construct and buffer were incubated for 24 h at 37° C. with mild agitation. After 24 h, the buffer was collected and assayed for BV-265 by an enzyme-linked immunosorbent assay (ELISA) specific for BV-265. The results are reported in FIG. 5 as quantity of BV-265 released into the buffer as a fraction of the total amount of BV-265 applied to the construct. As can be seen, EDC cross-linked constructs retain significantly more osteogenic material regardless of collagen or granule content. These data also show that an increasing content of CDHA granules, particularly beyond 150 mg/cc, improves retention of osteogenic material by the sponge compared to sponges with lower CDHA content.

Example 6

Effects of CDHA Surface Roughness on Cell Invasion

Colonization of CDHA granules by cells was investigated for collagen/CDHA constructs prepared as described herein containing granules of varying surface roughness ($R_a$) (FIG. 6). Constructs were implanted into rats at an intramuscular site along with 0.1 mg/mL BV-265 (BMP-GER-NR). Two weeks after implantation, the constructs were retrieved, fixed in formalin, decalcified, embedded in paraffin, sectioned, and stained with Goldner's Trichrome stain. Stained sections were examined microscopically for the presence of cells within the pore spaces of the granules and a cell invasion score (CI) was assigned based on the number of granules containing cells and the number of cells in each granule.

Figure 6A:
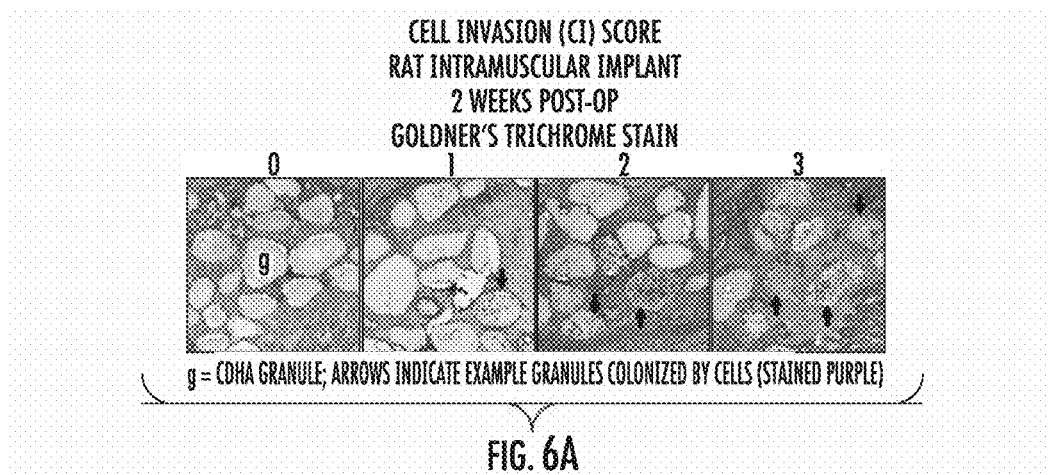
FIG. 6 shows the effect of surface roughness of CDHA granules contained within the implants on cell invasion. 6A and B show sections of implants two weeks post-implant, stained with Goldner's trichrome stain. 6C is a graph showing the relationship of surface roughness of the CDHA granules to cell invasion of the implants.
Figure 6B:
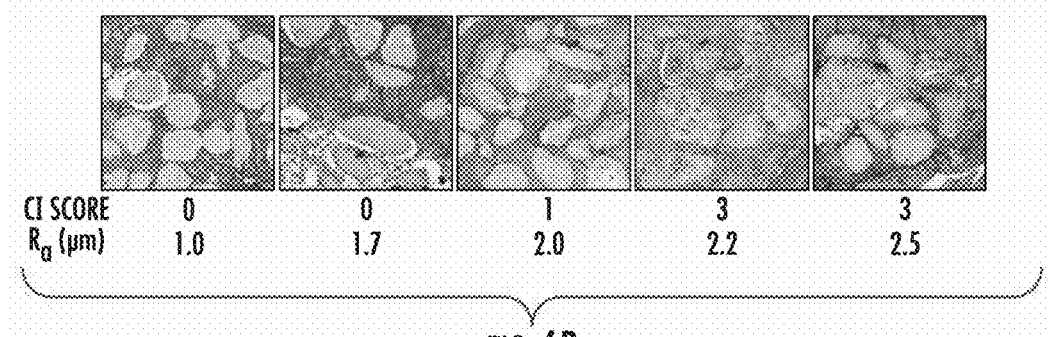
Figure 6C:
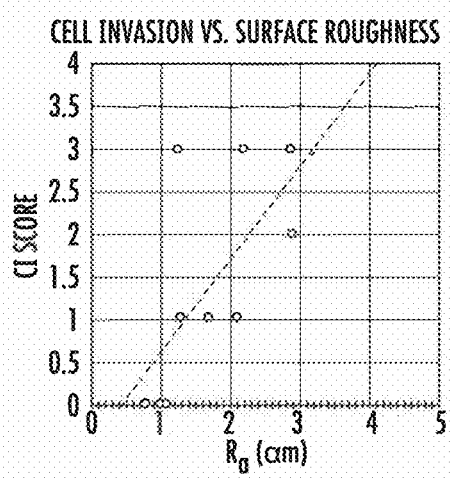

Stained sections are shown in FIGS. 6A and 6B and CI is plotted in FIG. 6C. As can be seen, the CI score increases with surface roughness of the granules. Definitions The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "consists essentially of" means excluding other materials that contribute to function, unless otherwise defined herein. Nonetheless, such other materials may be present, collectively or individually, in trace amounts.

As used in this specification, the term "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology.

Certain embodiments of the present invention have been described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A composition comprising a plurality of porous CDHA granules comprising macropores and micropores, said granules having a diameter in the range of from 425 to 800 µm, a specific surface area of greater than 50 $m^2/g$, a surface roughness (Ra) of at least 2.2 µm and a pH of 3.5 to 6.5; and wherein said plurality of granules has a tap density of less than 700 mg/cc; wherein said plurality of granules is admixed with a biocompatible matrix comprising an acidic collagen gel and an alkaline collagen powder, and wherein the collagen gel and collagen powder are present in the biocompatible matrix at a 1:1 ratio by dry mass.

2. The composition of claim 1, wherein the composition comprises from 150-200 mg/cc of said granules.

3. A bone graft substitute comprising a biocompatible porous carrier matrix comprising an acidic collagen gel and an alkaline collagen powder, wherein the collagen gel and collagen powder are present in the biocompatible matrix at a 1:1 ratio by dry mass and are cross-linked, said matrix having admixed therein a plurality of porous CDHA granules having a tap density of less than 700 mg/cc, and wherein said granules have a diameter in the range of from 425 to 800 µm, a surface roughness (Ra) of at least 2.2 µm and a pH of 3.5 to 6.5; and wherein said bone graft substitute is sterilized via exposure to E-Beam irradiation or ethyleneoxide.

4. The bone graft substitute of claim 3 further comprising an osteoinductive material, wherein said osteoinductive material is adhered to a plurality of the micropores and macropores and at least a portion of the outer surface of the granules.

5. A method of making a porous carrier matrix comprising the steps of:
   a. Forming a two-phase Type I collagen mixture comprising a water-swelled acidic collagengel and an alkaline collagen powder, and adjusting the mixture to an isotonic condition and neutral pH to form a biocompatible matrix material; wherein said collagen gel and collagen powder are mixed at a 1:1 ratio by dry weight;
   b. Adding a plurality of porous CDHA granules having a tap density of less than 700 mg/cc to said biocompatible matrix material to form a composite slurry, wherein said CDHA granules have a diameter of from 425-800 µm and comprise macropores and micropores, a surface roughness (Ra) of at least 2.2 µm, and a pH of 3.5 to 6.5;
   c. Shaping said composite slurry into a desired size and shape to form a shaped composite slurry and lyophilizing the shaped composite slurry to form a lyophilized composite material;
   d. Rehydrating the lyophilized composite material and adding a cross-linking agent to the lyophilized composite material to form a cross-linked composite material; and e. Lyophilizing the cross-linked composite materials prior to sterilizing the cross-linked composite material via exposure to E-Beam or ethylene oxide to form a sterilized composite material.

6. The method of claim 5, further comprising a step of exposing the sterilized composite material to a solution comprising an osteoinductive material under conditions sufficient to adhere the osteoinductive material to a plurality of the micropores and macropores and the outer surface of the granules.

* * * * *